United States Patent
Gegner et al.

(10) Patent No.: US 8,743,148 B2
(45) Date of Patent: Jun. 3, 2014

(54) METHOD OF OPTIMIZING THE PRESENTATION ON A DISPLAY SCREEN OF OBJECTS OF A USER INTERFACE WHICH CAN BE FREELY POSITIONED AND SCALED BY MEANS OF CONTROL ELEMENTS

(75) Inventors: Günter Gegner, Tübingen (DE); Harald Greiner, Nufringen (DE); Wilhelm Meier, Herrenberg (DE); Uli Tessel, Ehningen (DE)

(73) Assignee: Koninklijke Philips N.V., Eindhoven (NL)

( * ) Notice: Subject to any disclaimer, the term of this patent is extended or adjusted under 35 U.S.C. 154(b) by 2964 days.

(21) Appl. No.: 10/516,376

(22) PCT Filed: Jun. 4, 2003

(86) PCT No.: PCT/IB03/02100
§ 371 (c)(1),
(2), (4) Date: Nov. 30, 2004

(87) PCT Pub. No.: WO03/104966
PCT Pub. Date: Dec. 18, 2003

(65) Prior Publication Data
US 2005/0229110 A1    Oct. 13, 2005

(30) Foreign Application Priority Data
Jun. 6, 2002   (DE) .................................. 102 25 316

(51) Int. Cl.
*G09G 5/00*         (2006.01)
(52) U.S. Cl.
USPC ........................................... 345/660; 345/619
(58) Field of Classification Search
USPC ................. 345/619, 660, 661, 672, 676, 680; 715/788–789, 800, 243, 246, 252
See application file for complete search history.

(56) References Cited

U.S. PATENT DOCUMENTS

| | | | |
|---|---|---|---|
| 5,684,969 A | 11/1997 | Ishida | |
| 5,796,403 A | 8/1998 | Adams et al. | |
| 5,880,725 A | 3/1999 | Southgate | |
| 5,926,165 A * | 7/1999 | Grewer et al. | 715/800 |
| 6,111,573 A * | 8/2000 | McComb et al. | 345/661 |
| 6,707,476 B1 * | 3/2004 | Hochstedler | 715/789 |
| 6,950,993 B2 * | 9/2005 | Breinberg | 715/788 |
| 2003/0210281 A1 * | 11/2003 | Ellis et al. | 345/838 |

FOREIGN PATENT DOCUMENTS

| | | |
|---|---|---|
| EP | 0 820 002 | 1/1998 |
| WO | WO 00/63768 | 10/2000 |

OTHER PUBLICATIONS

Cohen, Ellis S., et al.; Automatic Strategies in the Siemens RTL Tiled Window Manager; Siemens Research & Technology Labs, Princeton, 1988.

* cited by examiner

*Primary Examiner* — Chante Harrison

(57) ABSTRACT

A presentation on a display screen of objects of a user interface which can be freely positioned and scaled by means of control elements is optimized. This is realized by a predetermined calculation rule in such a manner that the objects can be automatically varied between a still readable minimum size and a selected maximum size in dependence on the object contents, selected preferred settings and the available display resource on the display screen, and that the available display screen surface is optimally filled, possibly while eliminating less important details of the object contents and while changing the display mode of the object contents and/or the object as well as while avoiding mutual overlapping of the objects.

18 Claims, 7 Drawing Sheets

METHOD OF OPTIMIZING THE PRESENTATION ON A DISPLAY SCREEN OF OBJECTS OF A USER INTERFACE WHICH CAN BE FREELY POSITIONED AND SCALED BY MEANS OF CONTROL ELEMENTS

BACKGROUND

The invention relates to a method of optimizing the presentation on a display screen of objects of a user interface which can be freely positioned and scaled by means of control elements.

It is known that computers nowadays are operated via so-called user interfaces which present the functions of the associated operating system or its applications in the form of graphical objects (windows).

Because of their user friendliness, such user interfaces have become very popular notably in the private domain. For example, in this respect reference can be made to the graphical user interface "Microsoft Windows". But also in the technical domain, for example, generally also in the field of patient monitoring, graphical user interfaces are also frequently used, because these interfaces enable the simultaneous presentation of a plurality of objects on the display screen; for example, in the case of medical applications these objects relate to the blood pressure, the cardiac frequency or the like, and also represent graphically the variation thereof.

The user normally has the possibility of moving the objects on the surface of the display screen, to scale them and to configure the type of presentation, that is, to individually arrange a plurality of objects on the display screen. Manipulation of the object contents, that is, of the information to be displayed, however, is usually not at all possible or to a limited extent only. For example, if only the contents of a directory are to be displayed, the user automatically receives additional information in the form of the file size of the individual files. Automatic suppression of such additional information because of a limited display resource on the display screen is not possible. Consequently, the object contents and hence the information to be displayed remain the same.

The object contents also remain the same in the case of object scaling. For example, when the object is scaled down, additional scrolling lists are often provided on the side in order to enable continued viewing of the entire object contents. Automatic adaptation of the object contents, for example, in such a way that information which is less important because of the smaller representation is automatically suppressed, is not possible.

Matters are the same in the case of zooming of the object contents. Only a simple enlargement/reduction of the overall object contents by a predetermined factor then takes place. Adaptation of the object contents so that, for example, only a detail of the object contents is enlarged/reduced, is not possible.

Automatic adaptation of the user interface to a changing operating environment usually is not possible either. For example, when the computer is used as a measuring computer and the user has configured the user interface in such a manner that several measuring rows can be simultaneously displayed as objects and one of the measurements temporarily does not deliver results, only the latter is displayed as information. Automatic switching over of the display to another, available measuring row is not possible.

Granted, some user interfaces in the field of patient monitoring have facilities for limited adaptation to changing circumstances, but such user interfaces have the drawback that the user cannot individually adjust the size and position of the objects.

SUMMARY

Therefore, it is an object of the invention to provide a method of representing objects on a user interface which can be freely positioned and scaled by means of control elements, thus enabling optimum display of object contents while avoiding said drawbacks.

The disclosed techniques are based on the recognition of the fact that a calculation rule can be applied so as to transform the objects to be displayed into intelligent objects for the computer, thus ensuring optimum representation of the relevant objects or object contents in a user surface.

In accordance with one aspect, the objects can be automatically changed, in dependence on the object contents, the selected preferred settings and available display resources on the display screen, between a minimum size which can still be read and a predetermined maximum size by means of a selected calculation rule, that is, in such a manner that optimum filling of the available display screen surface is achieved, possibly while suppressing less important details of the object contents and while changing the display mode of the object contents and/or the object as well as while avoiding mutual overlapping of the objects. Such automatic adaptation of the objects holds in principle for all kinds of objects or object contents to be continuously presented on the user interface in a clearly arranged manner.

For example, the objects or the object contents may concern dynamically variable information, for example, temporal recordings of a measuring value, static information such as, for example, the output of a directory, as well as commands and various options for further processing/manipulation (also referred to as menu buttons hereinafter).

This is very advantageous in particular for patient monitoring, because the user, for example, a physician or a nurse, is continuously presented with all-important objects, such as selected patient information and associated menu buttons, in optimum readable form on the display screen for the purpose of further processing/manipulation. Thus, the time-consuming manual adjustment of the display screen surface is no longer necessary.

In accordance with another aspect, the objects are arranged within a fixed hierarchy so that when the display resource on the display screen is not sufficient, objects can be automatically suppressed, that is, starting with the lowest hierarchical level. As a result of the automatic suppression of less important objects, the display resource thus made available ensures a clearer display again of the remaining object contents on the display screen in a simple manner.

Because of the flexibility, the ordering of the hierarchically combined objects can be changed. For example, objects can be added or also be removed. However, the formation of intermediate hierarchies is also feasible, for example, in order to ensure more clarity in the case of a large number of hierarchically combined objects.

A plurality of objects can be combined so as to form a group in accordance with the invention. The combination of a plurality of objects so as to form a group offers the advantage that adjustments can be performed simultaneously for a plurality of objects in a simple manner. The respective adaptability is then maintained for the individual objects. For example, when a group of objects is reduced in such a manner that readability of all objects of this group is no longer ensured, less important objects of the group are automatically eliminated so as to ensure optimum readability of the remaining objects combined in the group. As an alternative for the suppression of individual objects in the group, the object representation of individual objects in the group can be changed, for example, a representation of individual objects as so-called switching surfaces. In that case such a switching surface again is a surface-optimized representation of the intelligent object only.

A preferred embodiment takes into account the behavior of the objects relative to one another and the interaction between a plurality of objects in relation to the display resource. This is very advantageous notably with a view to ease of operation and optimum use of the display resource. For example, when special settings are realized for a first object via menu functions, requiring a further adjustment via a menu function for a second object, the corresponding second menu for this second object is automatically displayed. Furthermore, for example, if a display on a larger display screen is desired, the adapted behavior of the objects relative to one another ensures automatic adaptation of the objects to the additional display resource. For example, objects, notably the previously described menu buttons, can also indicate pictograms in the case of an adequate display resource, which pictograms are automatically eliminated again when the display resource becomes inadequate.

In respect of the adapted behavior of the objects relative to one another, the further feature concerning automatic substitution of the objects amongst themselves is particularly advantageous. For example, if an object temporarily does not produce relevant data, a second object which delivers relevant data is automatically displayed instead.

In accordance with another aspect, the objects can be briefly displayed in enlarged form in dependence on a given trigger signal which is produced by a control element defined by an object selection/marking. This feature is particularly advantageous with a view to ease of operation. For example, when the user requires a given object, for example, a menu button or the like, the user can briefly display the objects in enlarged form on the user interface simply by "touching" by means of a cursor, thus enabling simplified selection.

Preferably, for the display of the objects on the display screen there are provided respective rectangular surfaces. The rectangular surfaces offer the advantage that the objects can be simply positioned on the display screen and that optimum use of the available display screen surface is ensured.

In conformity with a preferred embodiment, medical information, notably information for patient monitoring, is used as the object contents.

This application also relates to a device for the simultaneous compressed optical representation of the object data on a graphical user interface, which device includes an arithmetic unit for carrying out the method. The arithmetic unit is provided with a calculation program which optimizes the representation of object data in conformity with predetermined criteria in such a manner that, possibly while eliminating less important details of the object contents and while changing the mode of display of the object contents and/or the object as well as while avoiding mutual overlapping of the objects, the filling of the available display screen surface area is optimum.

Also provided is a control element for generating a trigger signal for the brief enlargement of selected/marked objects.

Also provided are input means whereby the display can be modified. The input means co-operate with medical measuring devices which form the statistic and dynamic information of the objects.

Further advantages and feasible applications of the present invention will become apparent from the following description which is given with reference to the embodiment shown in the drawing.

The invention will be described more or less schematically hereinafter on the basis of an embodiment for medical applications as shown in the drawing, however, without the invention being restricted thereto in any way.

BRIEF DESCRIPTION OF THE DRAWINGS

The terms and associated references as stated in the attached list of references will be used in the description, the patent claims, the abstract and the drawing. Therein:

DETAILED DESCRIPTION

Figure 1:
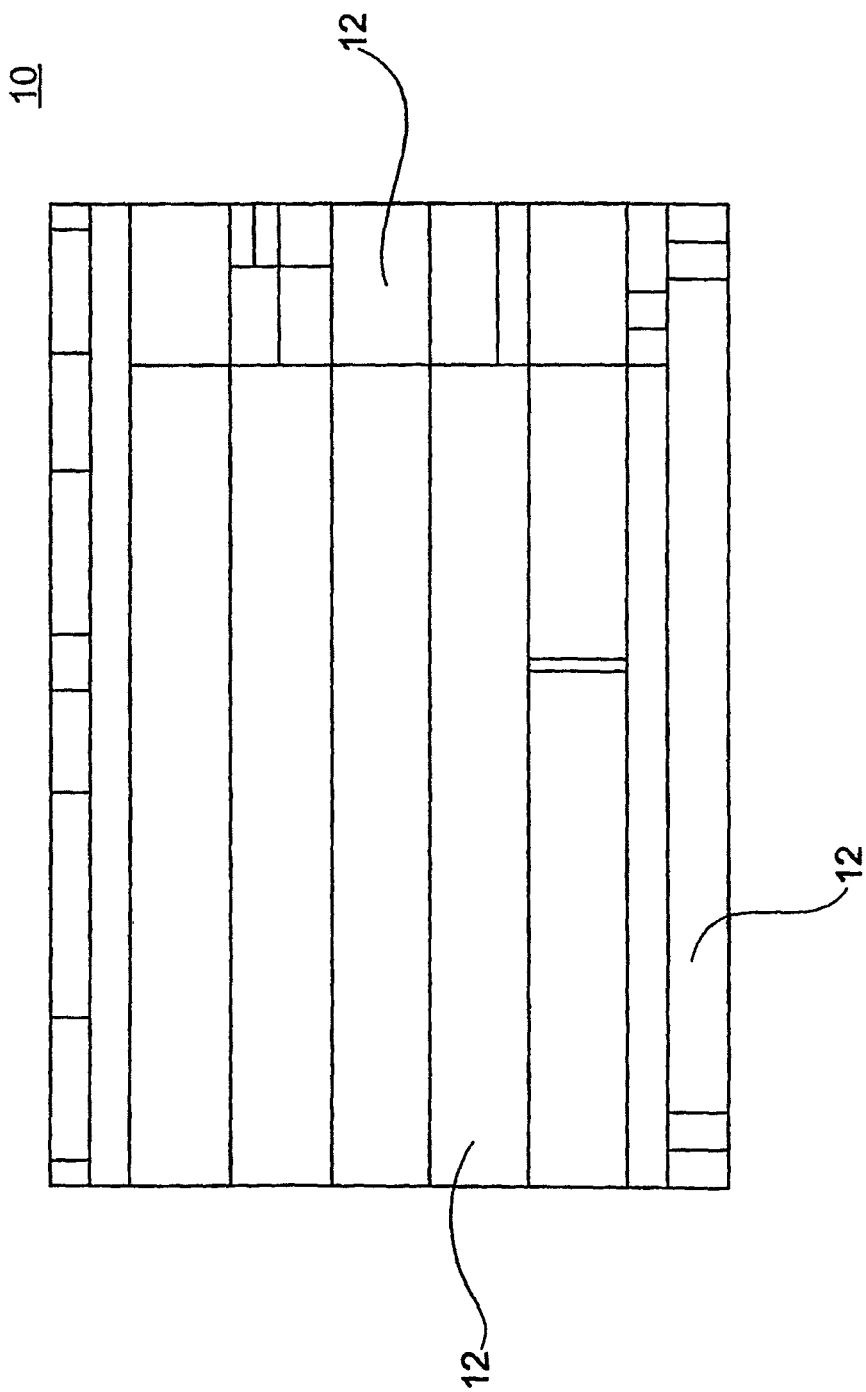
FIG. 1 is a diagrammatic representation of a plurality of objects of a user interface as used in the field of patient monitoring.

FIG. 1 shows a user interface 10 of the kind used for patient monitoring. The user interface 10 is composed of a plurality of rectangular objects 12. For the sake of clarity, only three objects are provided with a reference numeral 12 in FIG. 1.

The arrangement of the rectangular object 12 is chosen to be such that overlapping of individual objects is avoided. The surface area of the rectangular objects 12 corresponds each time to the space available for the representation of the contents of an object on the display screen surface (referred to hereinafter as the display resource).

The user interface 10, or the objects 12 of the user interface 10, can be individually configured at all times by means of special control elements (not shown here) such as a keyboard, a mouse, pens or the like, in a manner which is known per se. For example, the arrangement of the individual objects relative to one another can be adjusted at will and the size of the individual objects can also be scaled individually.

Figure 2:
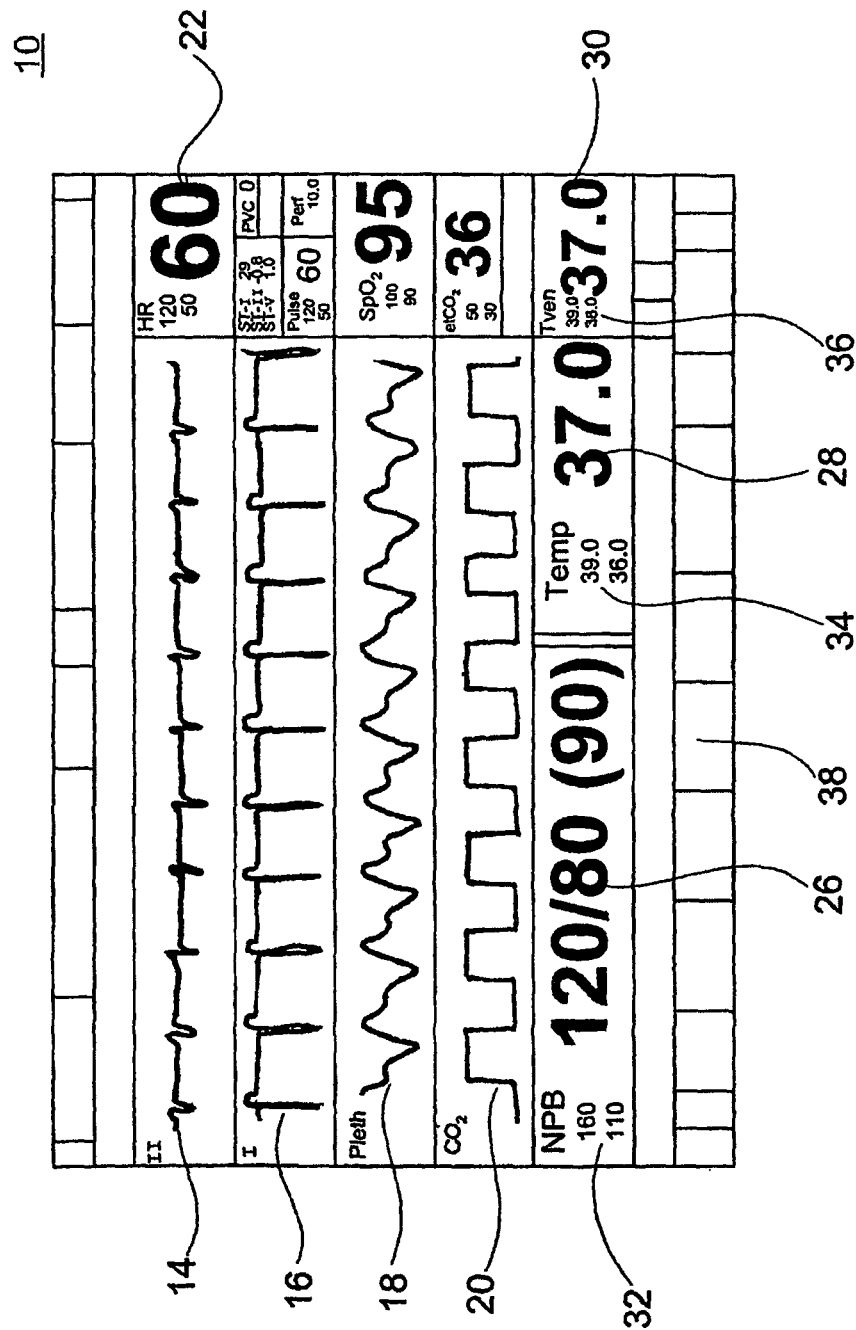
FIG. 2 shows the user interface of FIG. 1 with associated object contents.

FIG. 2 shows the user interface 10 of FIG. 1 with the associated object contents. As has already been stated, the objects to be displayed can be selected at will. In the present example inter alia a plurality of dynamically varying patient data, such as an ECG (electrocardiography) curve (derivative I) 14, a further ECG curve (derivative II) 16, an oxygen saturation curve 18 as well as a $CO_2$ respiratory curve 20, are shown in the form of curves. To the right of the curves 14, 16, 18 and 20 the corresponding curve values are shown in the form of a numerical display. For example, adjacent the ECG curve 14 there is shown the instantaneous cardiac frequency 22 with the associated alarm limits 24. The same holds for the curves 16 to 20.

Further patient information displayed on the user interface 10 concerns the blood pressure 26, a first body temperature 28 and a second body temperature (different measuring location) 30, together with the associated alarm limits 32, 34 and 36.

In order to carry out adjustments on the user interface 10, for example, a change of the alarm volume or the like, a plurality of objects 12 (referred to hereinafter as menu buttons 38) is provided in the lower region. The adjustment by way of the menu buttons can be carried out by means of various input means such as a keyboard, a mouse, pen elements or by touch screen input.

All of the objects 12 can be automatically changed by means of a calculation rule which controls the computer in such a manner that optimum filling of the available display screen surface is achieved in dependence on the object contents 14 to 38, selected preferred settings and available display resources on the display screen, possibly while suppressing less important details of the object contents and while varying the display mode of the object contents and/or the object as well as while avoiding mutual overlapping of the objects.

Because the objects 12 can thus be automatically changed, they can also be referred to as intelligent objects.

Figure 3:
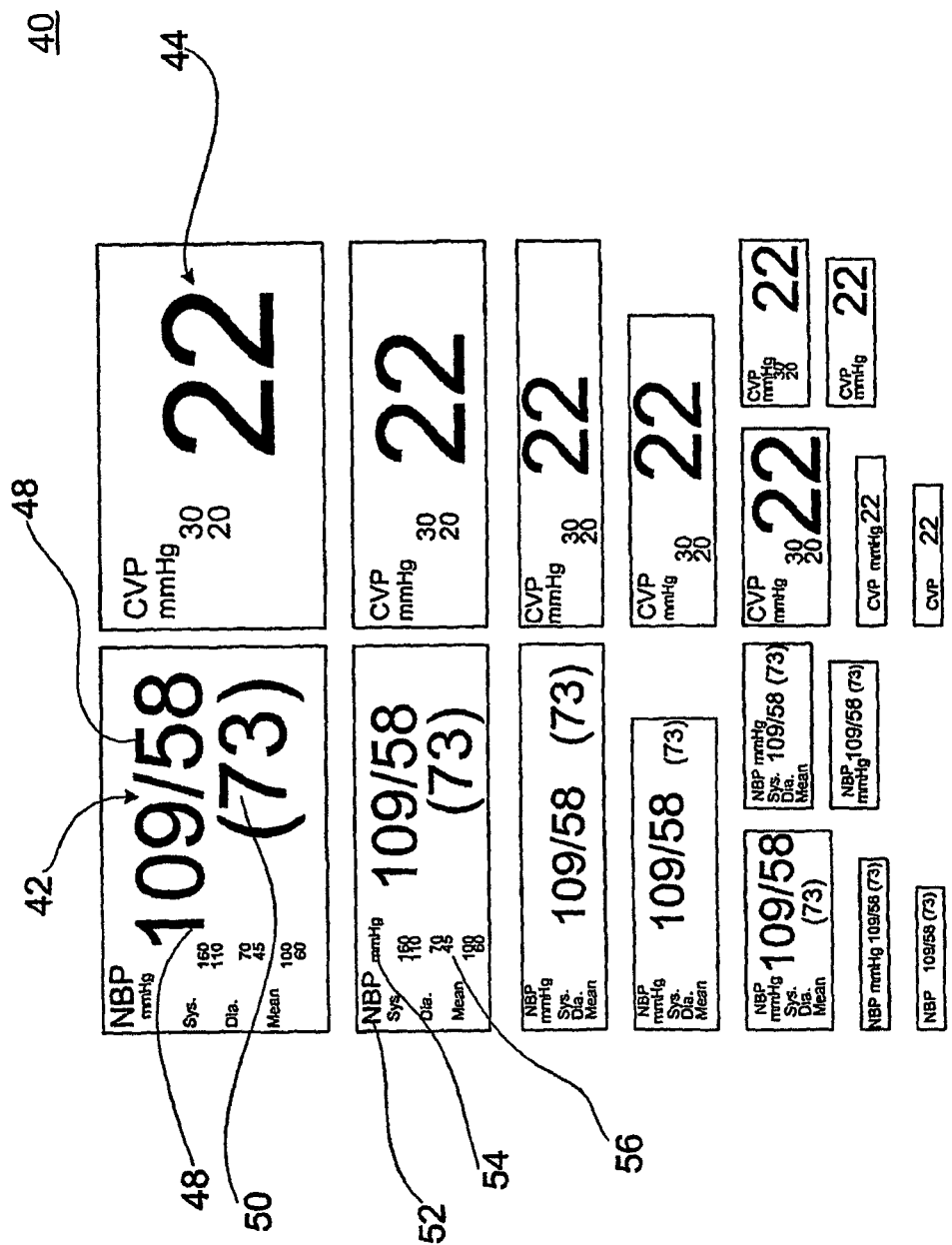
FIG. 3 shows two objects from a user interface which can be changed automatically.

FIG. 3 illustrates the variability of the representation of object contents as well as the suppression of less important detail information of object contents on the basis of two blood pressure displays 40.

Whereas in the left part of FIG. 3 various possibilities are given for display of a pulsating blood pressure indication 42, the right part of FIG. 3 shows various possibilities for display of a non-pulsating blood pressure 44.

Because it is recognized whether the blood pressure is pulsating, the display is automatically adapted in conformity with the display mode 42 or 44.

The various possibilities for display of the pulsating blood pressure 42 show, by way of example, how the object contents are adapted to a reduced object surface by means of a calculation rule.

The top left representation is the starting point of the description. The known and customary two-line blood pressure presentation comprises a systolic value 46, a diastolic value 48 as well as a mean value 50 which is stated between brackets. Furthermore, additional information is displayed in the form of an indication 52, a physical unit 54 as well as appropriate alarm limits 56. Because the values 46, 48 and 50 concern the central information, their display is clearly larger than that of the other information 52, 54 and 56.

If only a minor change of the display is required, the central information 46, 48 and 50 is scaled down in a simple manner, be it only to such an extent that good readability is still ensured. The other information 52, 54 and 56, already being shown at a smaller scale, however, retains its original size because a further reduction would lead to problems in respect of readability.

If a further reduction of the object surface is required, a change-over takes place automatically from the two-line display to a single-line display of the central information 46, 48 and 50. The other information 52, 54 and 56 still retains its original size as described previously. If an even smaller display of the object contents is required, automatic elimination of the less important other information, such as the physical unit 54 and the alarm limits 56, takes place as appears from FIG. 3.

The same holds for the display of the non-pulsating blood pressure 44. Again the object contents are first simply reduced. For the case where even less space is available for the object, a change of the object contents takes place by eliminating less important detail information as described above.

Figure 4:
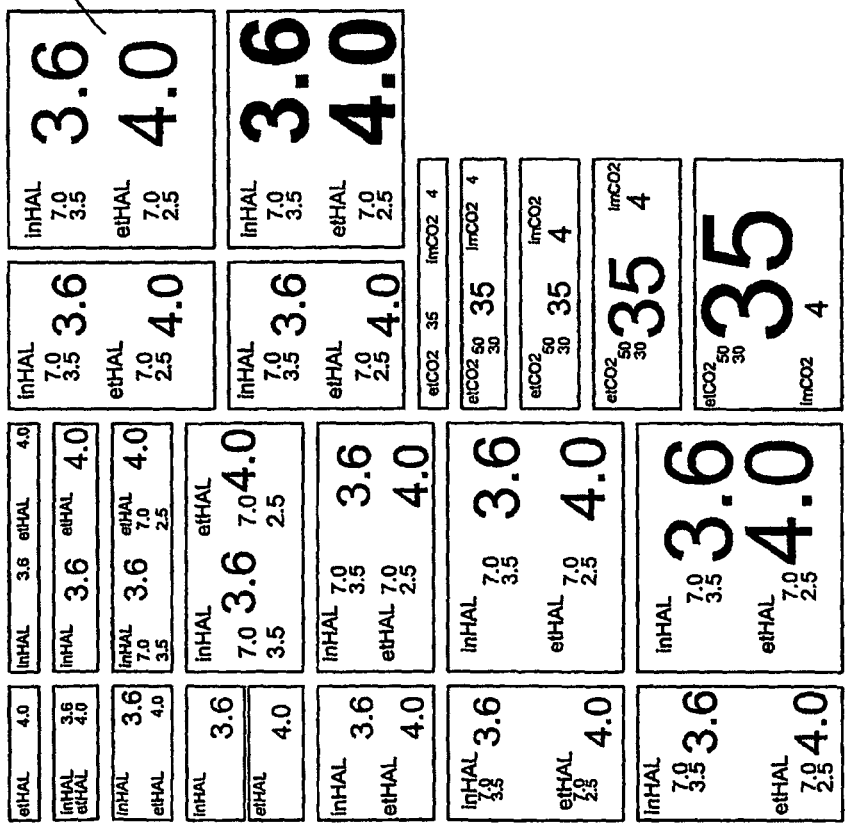
FIG. 4 shows a further object which can be changed automatically.
Figure 5:
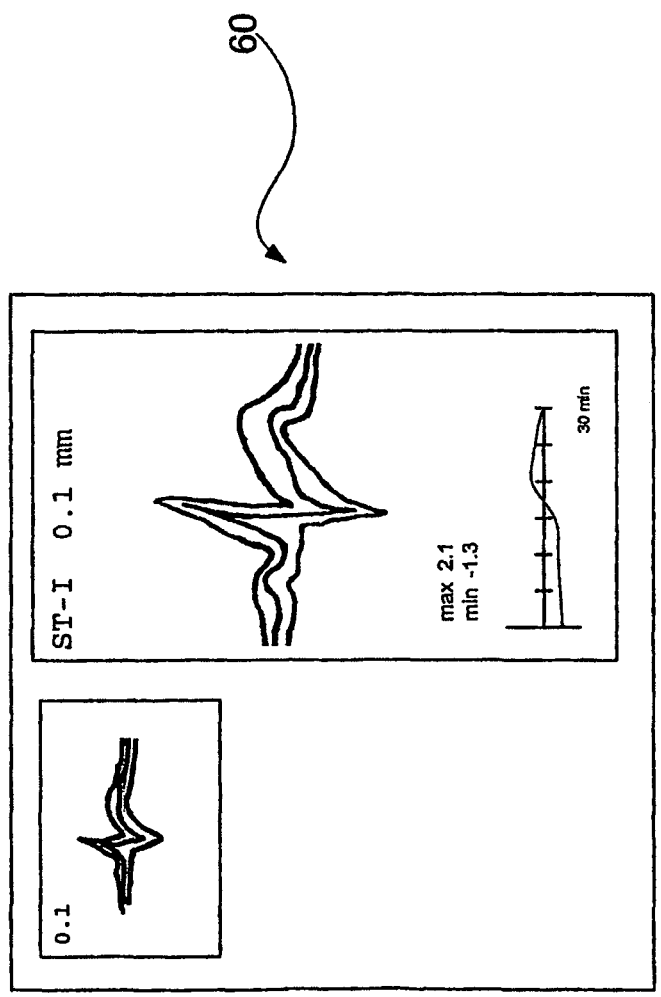
FIG. 5 shows a further detail of an object from a user interface for patient monitoring.

The FIGS. 4 and 5 show further examples of the adaptation of the objects 12 or the object contents to changing display resources. FIG. 4 again shows various possibilities for display of a numerical value, halothane and $CO_2$, each time for inhalation and exhalation 58, and FIG. 5 shows a variation of the ST segment in the electrocardiogram 60 with minimum and maximum deviation and the short term trend of the derived measuring value. FIG. 5 shows above all that the object contents can be displayed in different manners.

A plurality of objects 12 can be grouped together and put in hierarchical order. As a result, less important objects 12 can be eliminated, if necessary, for example, automatically. The additional display resource thus obtained is then used for optimized display of the remaining objects 12.

The combination of a plurality of objects so as to form a group makes sense notably when, for example, it is necessary to scale down/scale up a plurality of objects 12 simultaneously or to import these objects on a different display screen.

The automatic adaptation of objects 12, however, is not limited to the relevant object contents 14 to 36. For example, automatic adaptation of the objects 12, notably of the menu buttons 38 is possible (not explicitly shown) in dependence on the control element (mouse control as opposed to input via a rotary knob), the accuracy of the control element (touch screen input requires more object surface than input via a mouse cursor) and in dependence on the type of use (user is present in the direct vicinity of the user interface or in a more remote location).

These objects 12, such as menu buttons 38, can also be ordered in a hierarchical fashion and be structured in groups. In conformity with the foregoing description, this combined "control structure", notably its display, is then adapted exactly as simply as already described for the object contents 14 to 36. Depending on preference, the combined control structure can be displayed by means of simple scroll lists or in the form of columns.

Figure 6:
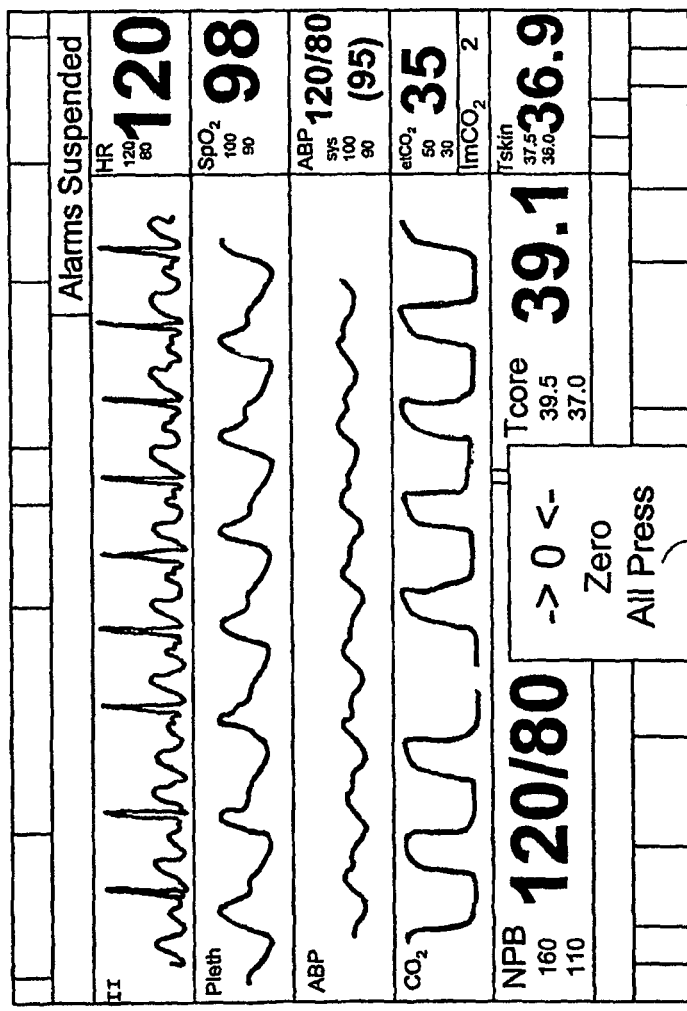
FIG. 6 shows another user interface from the field of patient monitoring with a briefly enlarged object.

FIG. 6 shows a further user interface 62 of the kind used for patient monitoring, that is, with a briefly enlarged object 64. The briefly enlarged object 64 is a menu button which, when touched by the cursor, is briefly assigned a larger display surface so that it can be better recognized from a distance. This briefly enlarged representation of an object can be used analogously for other objects. For example, it can be used as a "magnifying glass" for simplified reading of a measuring value.

Figure 7:
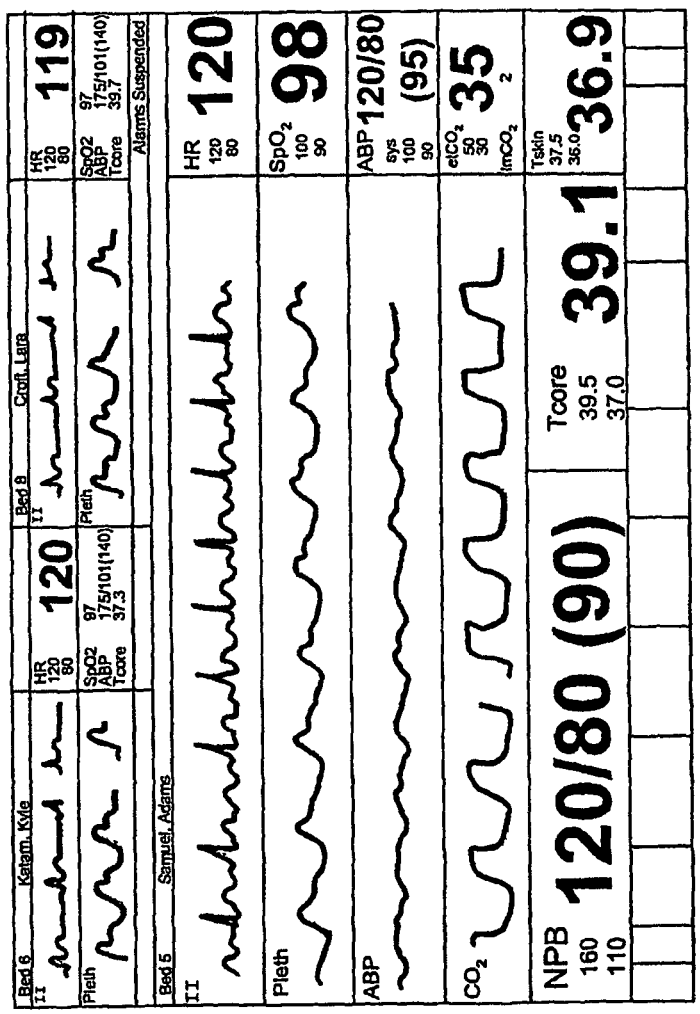
FIG. 7 shows a further user interface from the field of patient monitoring with a differently configured display.

FIG. 7 shows a further user interface 66 with a display configured in a different manner. FIG. 7 demonstrates above all the flexibility with which the various objects 12 can be displayed. For example, in this user interface 66 not only information concerning a single patient is displayed. The upper region of the user interface 66 also contains information concerning other patients. To this end it was merely necessary to combine each time the necessary objects so as to form a group. The optimum display of the grouped objects after import in the user interface 66, however, takes place automatically by means of the selected calculation rule as has already been described.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of changing a mode of a presentation of a plurality of rectangular objects on a display screen, each object containing at least one of alphanumeric characters or a curve indicative of patient information from a medical monitor, the method comprising, with a computer processor:

sizing and displaying the plurality of objects on the display such that the objects fill the display screen without overlapping;
receiving a designation of one or more of the objects to be enlarged;
in response to the designation, enlarging the one or more designated objects and reducing at least one non-designated object such that the objects fill the display screen without overlapping, the reducing including deleting one or more alphanumeric characters or curves in a preselected order such that remaining alphanumeric characters and curves have at least a preselected minimum size.

2. The method as claimed in claim 1, further including:
suppressing detail in the other objects to maintain the preselected minimum size.

3. A method of changing a mode of a presentation on a display screen of objects of a user interface, the method comprising:

generating a plurality of objects, each object containing at least one of a curve or alphanumeric character indicative of patient information from a medical measuring device;
positioning and scaling the objects to form at least a first group of objects corresponding to a first patient and a second group of objects corresponding to a second patient in such a manner that the objects can be automatically changed, in dependence on object contents, selected preferred settings and an available display surface resource on the display screen, between a selected minimum size and a selected maximum size in such a manner that filling of the available display screen surface is achieved, without mutual overlapping of the objects, wherein the positioning and scaling includes at least one of:
  resizing the objects of the first group relative to the objects of the second group and displaying the objects of the first and second groups without overlapping, and
  designating one of the groups and enlarging the objects of the designated group and displaying the objects of the first and second groups without overlapping;
concurrently displaying the first and second groups of objects on the display screen.

4. The method as claimed in claim 3, further including:
automatically substituting the objects among themselves.

5. The method as claimed in claim 3, further including:
generating a cursor on the display screen;
with the cursor, designating one of the objects; and,
temporarily enlarging the designated object and reducing a size of other objects such that the enlarged and other objects fill the available display screen surface without overlapping.

6. The method as claimed in claim 3, further including:
in response to one of the objects ceasing to contain patient monitoring information, automatically, without user intervention, substituting another object for the one object.

7. The method as claimed in claim 6, further including:
in response to the another object being substituted, automatically repositioning and rescaling the objects to fill the available display screen surface without overlapping.

8. A method of changing a mode of presentation of objects on a display screen of a user interface, the objects including menu buttons and objects which contain at least one of alphanumeric characters and waveforms indicative of patient physiological information from medical monitors, the method comprising:

automatically displaying the objects on the display screen such that the objects fill the display screen without overlapping and such that the alphanumeric characters and the waveforms have at least a preselected minimum size and such that all available physiological information from the monitors is not displayed;
adding a new object displaying at least some of the available and previously not displayed physiological information;
resizing the objects such that the objects fill the display screen without overlapping and such that the alphanumeric characters and waveforms have at least the preselected minimum size.

9. The method as claimed in claim 8, further including:
touching a selected object with a cursor;
temporarily enlarging the selected object when it is touched by the cursor;
reducing the size of other objects including removing at least one of the alphanumeric characters, the waveforms, and the objects such that the remaining alphanumeric characters and waveforms have the preselected minimum size such that the objects fill the display screen without overlapping; and
returning the enlarged object to its original size when the cursor no longer touches the enlarged object and resizing the other objects.

10. The method as claimed in claim 8, wherein the new object is substituted for a previously displayed object which previously displayed object is removed from the display screen.

11. A method of changing a mode of a presentation of static and dynamic objects containing patient monitoring information, the method comprising:

generating a plurality of objects, each object containing patient monitoring information from a medical measuring device;
positioning and scaling the objects in a group in such a manner that the objects are automatically changeably positioned and scaled in dependence on object contents, selected settings, and fill available display resources on a display screen while avoiding overlapping objects;
in response to one of the objects ceasing to contain patient monitoring information, automatically, without user intervention, substituting another object and repositioning and rescaling the displayed objects such that the rescaled objects fill the available display resources on the display screen while avoiding overlapping.

12. The method as claimed in claim 11, wherein the objects are arranged within a fixed hierarchy and the objects are sized based on relative hierarchical level.

13. The method as claimed in claim 11, further including:
generating a cursor on the display screen;
moving the cursor on the display screen using a user input device;
in response to touching one of the objects with the cursor, temporarily enlarging the touched object and reducing or deleting other objects such that displayed objects fill the available display resources on the display screen while avoiding overlapping.

14. The method as claimed in claim 11, wherein the patient monitoring information is displayed in at least one of alphanumeric characters and waveforms and wherein the repositioning and rescaling includes automatically eliminating at least some of the alphanumeric characters, the waveforms, or the objects such that the remaining displayed alphanumeric characters and waveforms have at least a preselected minimum size.

15. A method of changing a mode of presentation of a selected plurality of objects on a display screen of a user interface, the method comprising:
displaying the selected objects on the display screen such that an available display screen surface is filled without overlapping the displayed objects, the objects including menu buttons and physiological data objects which contain alphanumeric characters and waveforms indicative of physiological values of a patient, the alphanumeric characters and the waveforms being displayed with at least a preselected minimum size;
in response to a trigger signal, automatically enlarging a first of the objects indicated by the trigger signal and automatically resizing and repositioning the other objects such that the available display screen surface is filled without overlapping the displayed objects including eliminating at least one of the alphanumeric characters, or at least one of the waveforms, or at least one of the objects such that the displayed alphanumeric characters and waveforms in all displayed objects are displayed with the preselected minimum size.

16. The method as claimed in claim 15, wherein respective rectangular surfaces are provided for the display of the objects on the display screen.

17. The device as claimed in claim 15, wherein the first object is temporarily enlarged and then the objects return to their sizes and positions before the enlarging of the first object.

18. A device for changing a presentation of static and dynamic objects containing dynamically varying patient data, the device comprising:
a display screen on which the objects are presented;
an interface which receives dynamically varying patient data and displays the patient data in objects on the display screen, the interface being configured to:
substitute, reposition, and rescale the displayed objects in response to one of the displayed objects ceasing to receive at least some of the patient data, and
position and scale the displayed objects to automatically change object contents, settings, and available resources on the display screen, and
avoid overlapping of the displayed objects.

* * * * *